United States Patent
Cardelius et al.

(10) Patent No.: US 6,817,250 B2
(45) Date of Patent: Nov. 16, 2004

(54) ACOUSTIC GAS METER WITH A TEMPERATURE PROBE HAVING AN ELONGATED SENSOR REGION

(75) Inventors: Erik Cardelius, Stockholm (SE); Lars Skoglund, Sollentuna (SE)

(73) Assignee: Maquet Critical Care AB, Solna (SE)

( * ) Notice: Subject to any disclaimer, the term of this patent is extended or adjusted under 35 U.S.C. 154(b) by 0 days.

(21) Appl. No.: 10/329,934

(22) Filed: Dec. 26, 2002

(65) Prior Publication Data

US 2003/0136200 A1 Jul. 24, 2003

(30) Foreign Application Priority Data

Jan. 24, 2002 (SE) ............................................. 0200184

(51) Int. Cl.[7] ................................................ G01F 1/66
(52) U.S. Cl. ................................................ 73/861.27
(58) Field of Search .................... 73/861.27, 861.28, 73/861.29, 204.12

(56) References Cited

U.S. PATENT DOCUMENTS

| | | | |
|---|---|---|---|
| 5,247,826 A | | 9/1993 | Frola et al. |
| 5,645,071 A | * | 7/1997 | Harnoncourt et al. ........ 600/532 |
| 5,987,992 A | * | 11/1999 | Watanabe et al. .............. 73/632 |
| 6,305,233 B1 | * | 10/2001 | Braathen et al. .......... 73/861.28 |
| 6,425,293 B1 | * | 7/2002 | Woodroffe et al. ............ 73/756 |
| 6,485,175 B1 | * | 11/2002 | Nimberger et al. ......... 374/142 |
| 6,487,904 B1 | * | 12/2002 | Myhre ...................... 73/204.12 |

FOREIGN PATENT DOCUMENTS

| | | |
|---|---|---|
| EP | 1 083 427 | 3/2001 |
| SE | 510435 | 5/1999 |
| WO | WO 88/05160 | 7/1988 |
| WO | WO 92/03724 | 3/1992 |

* cited by examiner

Primary Examiner—Edward Lefkowitz
Assistant Examiner—Jewel V. Thompson
(74) Attorney, Agent, or Firm—Schiff Hardin LLP

(57) ABSTRACT

An acoustic gas meter has an acoustic transmitter/receiver arrangement disposed within a gas flow conduit for transmitting and receiving acoustic energy along an acoustic path. A temperature probe has an elongate sensor region disposed relative to, preferably along, the acoustic path to provide a measure of a gas temperature indicative of an average gas temperature within the acoustic path.

6 Claims, 3 Drawing Sheets

ACOUSTIC GAS METER WITH A TEMPERATURE PROBE HAVING AN ELONGATED SENSOR REGION

BACKGROUND OF THE INVENTION

1. Field of the Invention

The present invention relates to an acoustic gas meter and in particular to a meter for the analysis of proportions of gases in gas mixtures.

2. Description of the Prior Art

In medical and clinical settings it is useful to be able to measure accurately the concentrations and/or flow rates of respiratory (inspiration and/or expiration) gases or changes therein since these can provide, for example, valuable information on patient metabolic conditions. This is particularly the case during the provision of mechanical respiratory aid to a patient where knowledge of the relative and absolute amounts of oxygen and carbon dioxide within the expiration gas may be used to provide information on the metabolization of oxygen as well as respiratory function. Moreover, knowledge of the oxygen/nitrogen ratio in an inspiration gas is useful for controlling or monitoring the provision of mechanical respiratory aid.

Known acoustic gas meters have an ultrasonic transducer arrangement adapted to transmit ultrasound pulses along an acoustic path through a gas mixture within a measurement cell or a section of a flow conduit containing the flowing gas mixture and to receive the transmitted pulses; and a calculation unit for calculating the transit time of the ultrasound pulses. The transit time calculated in this manner may be used in known techniques to provide a measure of the flow and, additionally or alternatively, the composition of the gaseous medium. Because the velocity of sound through a gaseous medium is known to be dependent on the temperature of that medium then a temperature probe is often included as part of the meter to monitor the gas temperature at a point within the cell or section and to provide this temperature to the calculation unit where it may be employed to compensate the calculated parameters for temperature variations.

Gas meters are known, for example from PCT Application WO 92/03724 and from U.S. Pat. No. 5,247,826, for acoustically analyzing the ratios of a mixture of gases comprising two known gases, such as the oxygen/nitrogen ratio in a breathing gas to be supplied to a patient from which the oxygen concentration or changes therein can be determined. Such known meters utilize the physical phenomenon that acoustic waves travel with different velocities through different gases. The velocity of sound, V, through a gas is known to be proportional to $(T/M)0.5$ where M is the molecular weight of the gas and T is its absolute temperature. Thus for a gas mixture at a known temperature the velocity of sound, V, in the mixture can be used to provide a measure of the relative concentrations of the constituents of the gas.

However, the temperature of the gas will vary according to its pressure so that in circumstances where the gas has a variable and rapidly changing pressure, such as typically found in inspiration and expiration gases during mechanical respiratory aid, inaccuracies in the measured gas ratio can occur (typically a 10C error in temperature will give approximately a 3% error in oxygen concentration in a binary gas mixture with air). This is particularly problematical when the pressure induced temperature variation causes a temperature gradient to occur within the acoustic path through the gas mixture to be analyzed.

SUMMARY OF THE INVENTION

The above object is achieved in accordance with the principles of the present invention in an acoustic gas meter having an acoustic transmitter/receiver arrangement for transmitting and receiving acoustic energy along an acoustic path, and a temperature probe having a sensor region disposed to measure a gas temperature, said sensor region being elongate and disposed relative to the acoustic path to provide a measure of a gas temperature indicative of an average gas temperature within the acoustic path.

By providing a temperature probe having an extended sensor region, for example by using a number of point sensors with a known spatial interrelationship or, more simply, by employing a length wire of known temperature versus electrical resistance characteristics, then the average temperature of gas within the acoustic path traversed by the acoustic energy can be monitored. In this manner a temperature measurement can be made which more accurately reflects the temperature of the actual gas through which the emitted acoustic energy propagates.

The length of wire may be provided with one or more bends so as to form, for example, a wire loop, spiral or zigzag pattern, so that the total length of wire employed as the sensor region is longer than the acoustic path length. This leads to an increased electrical resistance change per degree of temperature change and so reduces any signal amplification requirements.

DESCRIPTION OF THE PREFERRED EMBODIMENTS

Figure 1:
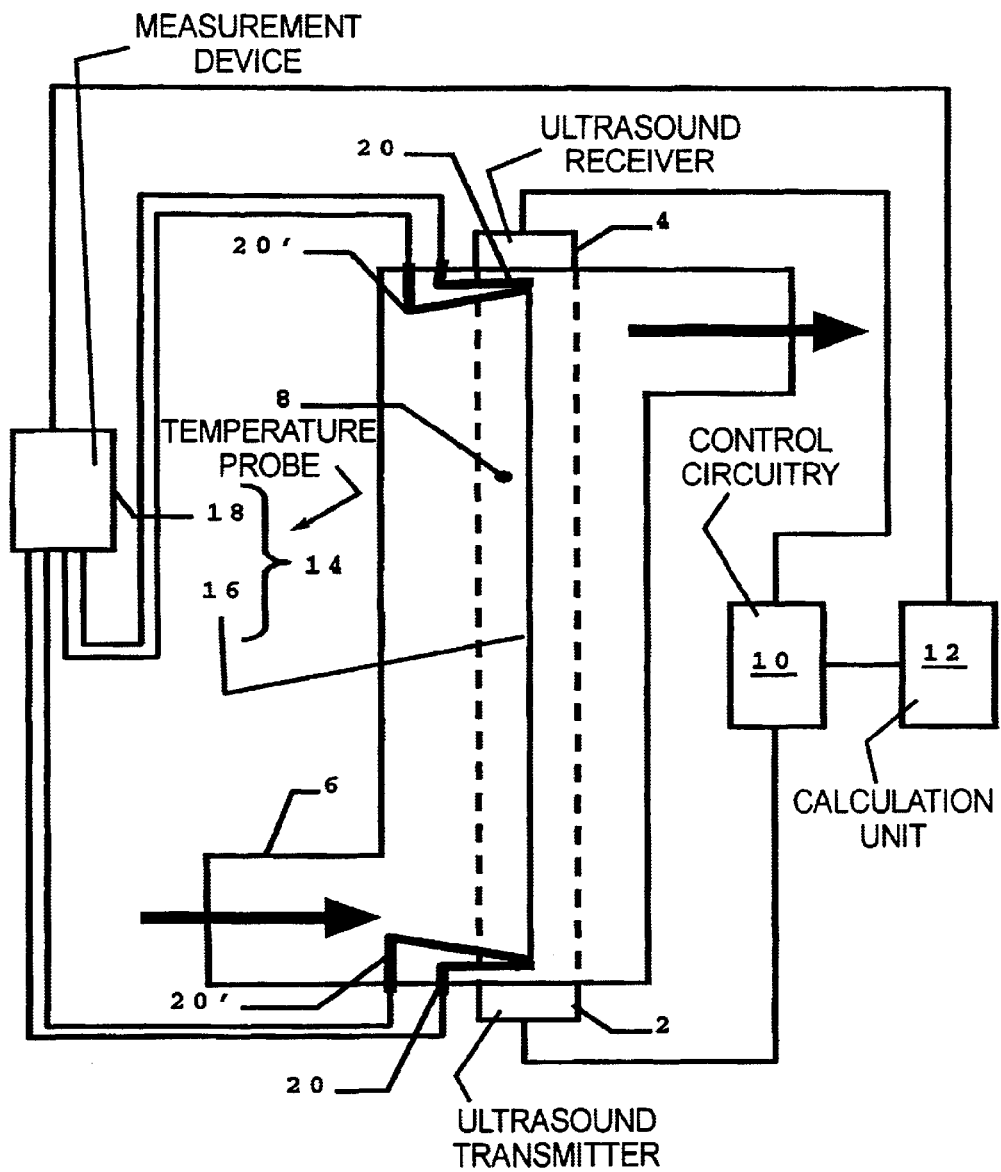
FIG. 1 is a schematic illustration of a first embodiment of an acoustic gas meter according to the present invention.

Considering now the gas meter of FIG. 1, an ultrasound transmitter 2 and a complementary receiver 4 are disposed in ultrasonic coupling with a gas flow conduit 6 to define opposite ends of an acoustic path 8 (shown as broken lines). Electronic control circuitry 10 is provided in operable connection with each of the ultrasound transmitter 2 and receiver 4 and is configured to cause the transmitter 2 to emit an ultrasound signal. The receiver 4 detects the emitted ultrasound signal after it traverses the acoustic path 8. The control circuitry 10 measures the elapsed time between the emission and the detection of the ultrasound signal. A calculation unit 12, as may be realized in a suitably programmed microcomputer, is connectable with the electronic circuitry 10 with which it co-operates to receive a signal indicative of the measured elapsed time. In the described embodiment the gas flows through the conduit 6 in only one direction (for example as shown by the arrows in FIG. 1) and the ultrasound signal traverses the acoustic path 8 in only one direction, from transmitter 2 to receiver 4 so that a measured acoustic velocity, $V_m$, will be affected by the flow velocity, Vg, of the gas (in the present example increased so that $V_m = V + V_g$). The calculation unit 12 is configured to determine, in a known manner, the gas flow velocity, $V_g$, of gas flowing within the acoustic path 8 from the received signal and from a measure of the temperature, T (from V being proportional to $(T/M)^{0.5}$), of a gas of a known composition within the flow path 8. The temperature T is obtained from a temperature probe 14 according to the present invention and described in more detail below.

Such an arrangement is well known in the art and is described herein only in sufficient detail to enable a skilled person to properly appreciate the present invention. It will be appreciated that each of the dedicated ultrasound transmitter 2 and receiver 4 may be substituted with an ultrasound transceiver and the electronic circuitry 10 non-inventively adapted to cause each transceiver 2,4 to act in turn as a receiver in a complementary transmitter and receiver arrangement. This enables the transmission and subsequent detection of ultrasound traveling in either direction along the acoustic path 8. Since flow velocity Vg of the gas will affect the acoustic velocity V in an equal but opposite manner for the different directions of travel of the ultrasound signal the calculation unit 12 may then be configured to determine, in a known manner, a value of the acoustic velocity, V, that is independent of the gas flow velocity $V_g$ by the appropriate combination of the acoustic velocities measured for each of the two directions of travel of the acoustic signal. In this arrangement the calculation unit 12 can also be configured to determine, in a known manner, a flow velocity of the gas Vg independent of a knowledge of the temperature T of the gas within the acoustic path 8 and additionally or alternatively, knowing the temperature T, a gas composition if the magnitude of one of the components of the gas within the acoustic path 8 is unknown.

The temperature probe 14 according to the present invention is shown in FIG. 1 as including a sensor region formed by a length of wire 16, such as platinum wire, having know temperature versus electrical resistance characteristics, which extends straight along substantially all of the acoustic path 8, and a measurement device 18 for measuring the resistance of the wire 16 and for providing an output indicative thereof to the calculation unit 12. Such a measurement device 18 may, for example, include a balanced bridge arrangement of the type typically employed to measure resistance in conventional platinum-resistance thermometers. The platinum wire 16 is relatively thin (in the present example 17.8 µm diameter) so as to provide an adequate response time to rapid pressure induced temperature changes within the gas and is connected at its opposite ends, at the transmitter 2 and receiver 4, to pairs 20, 20' of larger diameter wires (in the present example 50 µm) which preferably extend through gas within in the conduit 6 in order to achieve substantially the same temperature as that of the platinum wire 16. These pairs 20, 20' of wires are provided for electrical connection to the measurement device 18 in a standard "four-wire" arrangement.

As an alternative, the length of wire 16 need not be located in the acoustic path 8 itself but may be located in another region of the conduit 6 in which the average temperature, as sensed by the sensor region formed by the wire 16, is the same as or has a known relationship to the temperature along the acoustic path 8. In the circumstance in which the temperature sensed by the sensor region of the wire 16 has a known relationship then the calculation unit 12 may be further configured to determine the temperature along the acoustic path 8 using the sensed temperature and the known relationship. This relationship may readily be determined empirically, for example by a comparing the instantaneous temperatures for the flow path and for the wire 16, perhaps under different flow conditions. Thus the temperature probe 14 of this alternative actually provides a measure of a temperature indicative of that along the acoustic path 8.

Figure 2:
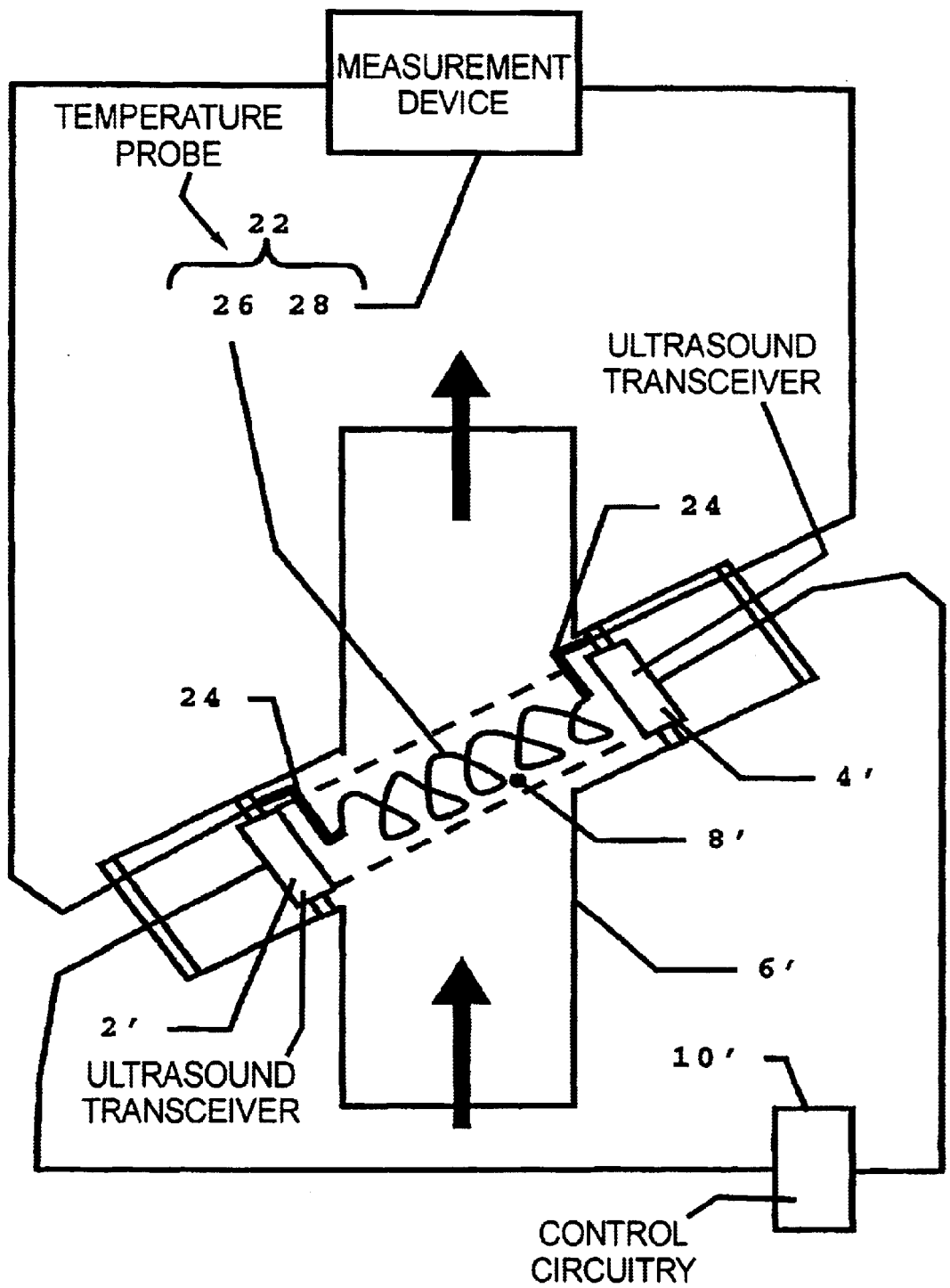
FIG. 2 is a schematic illustration of a second embodiment of an acoustic gas meter according to the present invention.

FIG. 2 illustrates an acoustic gas analyzer in which the acoustic transceivers 2',4' are arranged to define an acoustic path 8' which is at an angle to the direction of gas flow (illustrated by arrows) through the gas flow conduit 6' and are controlled to alternatively operate as complementary transmitter and receiver by means of conventional control circuitry 10'. As with the control circuitry 10 of FIG. 1, the circuitry 10' includes means for determining a transit time for acoustic energy passing between the transceivers 2'4', along the acoustic path 8' in each direction. The determined transit times are used within a calculation unit (not shown) in the determination of one or both of the flow velocity Vg of the gas and the composition of the gas within the acoustic path 8', according to methodology well known in the art. The transceiver 2'4' geometry of FIG. 2 is well known in the art of acoustic gas flow measurement and is described in greater detail in, for example, U.S. Pat. No. 6,098,467.

In order to enhance the resistance (or other measured electrical property) change with temperature over the temperature probe 14 of FIG. 1 a temperature probe 22 is substituted in which the wire 26 forming the sensor region is provided with a number of bends, in this example forming into a spiral, and is preferably disposed along the acoustic path 8 (See FIG. 2).

The wire 26 is connected at opposite ends, at the transceivers 2', 4', to electrical conductors 24. These conductors 24 are, in turn, arranged for electrical connection with a measurement device 28 which provides an output dependent on the resistance of the wire 26. It will be appreciated that these conductors 24 can be substituted with or substitute for the two pairs of wires 20, 20' in the temperature probe 14 of FIG. 1 and the measurement devices 18, 28 adapted accordingly.

It will be further appreciated that other shapes for the wire 26 may be devised so that the total length of the wire 26 is greater than the length of the acoustic path 8' and still be within the scope of the invention as claimed.

Figure 3:
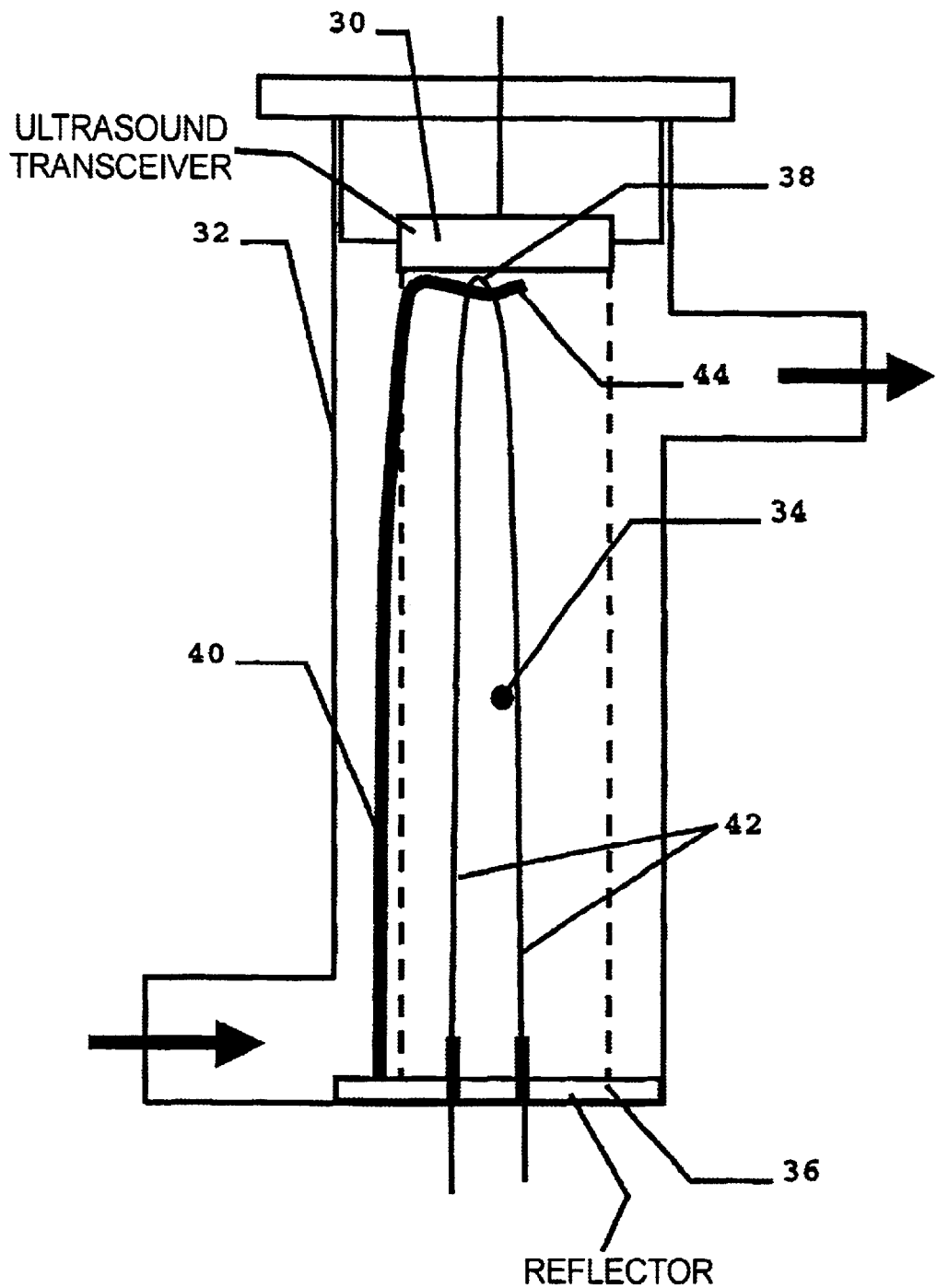
FIG. 3 is a schematic illustration of a third embodiment of an acoustic gas meter according to the present invention.

Referring now to FIG. 3, an ultrasound transceiver 30 is disposed within a gas flow conduit 32 to delimit an end of an acoustic path 34 and is capable of being operated alternately as an ultrasound transmitter and a receiver when connected to appropriate known control circuitry (not shown). An ultrasound reflector 36, which may be a part of or, as illustrated in FIG. 3, different from the conduit 32, is positioned to define an opposite end of the acoustic path 34. The reflector 36 is arranged to reflect incident ultrasonic energy that is emitted from the transceiver 30 when operated as a transmitter back to the transceiver 30 where it is detected when operated as a receiver.

A wire 38, which acts as the sensor region of a temperature probe, enters the acoustic path 34 at the end that is delimited by the reflector 36, passes along the path 34, is looped over a support structure 40 toward the end of the acoustic path 34 that is proximal the transceiver 30, and is terminated at the end of the acoustic path 34 at which it entered. As with the temperature probes 14;22 of the previously described embodiments the wire 38 may, alternatively, be located outside the acoustic path 34 in a region having a known temperature relationship with the path 34. The sensor region so defined by the wire 38 is thus substantially twice as long as the acoustic path 34. Preferably, the two "legs" 42 of the wire loop 38 are arranged substantially parallel to one another and to the side walls of the conduit 32 that surround the acoustic path 34. In this manner the effects of any temperature gradient perpendicular to the direction of travel of the acoustic energy between transceiver 30 and reflector 36 are reduced.

The support structure 40 is, in the present example, shown to extend from a region of the conduit 32 proximal the reflector 36 and should be thermally insulated, at least along the section 44 which contacts the wire 38, so as to help reduce the thermal effects of the support 40 on the response of the wire 38 to rapid (for example pressure induced) changes in the gas within the acoustic path 34.

It will be appreciated by those skilled in the art that the response time of the temperature probes of the present invention, such as are illustrated in the above exemplary embodiments, will depend to a large extent on the thickness of the wires that form the sensor regions, Thus the thinner the wire the faster the response time will be and may be selected dependent on the intended use of the acoustic gas meter according to the present invention. It will also be appreciated that acoustic energy other than ultrasound may be employed in accordance with the invention.

Although modifications and changes may be suggested by those skilled in the art, it is the intention of the inventors to embody within the patent warranted hereon all changes and modifications as reasonably and properly come within the scope of their contribution to the art.

We claim as our invention:

1. An arrangement for loading rate table data comprising:

an acoustic transmitter/receiver arrangement for transmitting and receiving acoustic energy along an acoustic path, said acoustic energy exhibiting a transit time in said acoustic path;

a single temperature probe having an elongate sensor region disposed relative to said acoustic path to measure a gas temperature indicative of an average gas temperature within said acoustic path; and a calculation unit for identifying a characteristic of gas in said acoustic path from said transit time and said average gas temperature.

2. An acoustic gas meter as claimed in claim 1 wherein said sensor region of said temperature probe extends along said acoustic path.

3. An acoustic gas meter as claimed in claim 1 wherein said sensor region comprises a length of wire having a known temperature versus electrical resistance characteristic.

4. An acoustic gas meter as claimed in claim 3 wherein said wire has at least one bend so that said wire length is longer than a length of said acoustic path.

5. An acoustic gas meter as claimed in claim 4 wherein said at least one bend is disposed to traverse said acoustic path twice.

6. An acoustic gas meter as claimed in claim 5 wherein said acoustic transmitter/receiver arrangement comprises an acoustic transceiver and a reflector disposed opposite said transceiver to reflect acoustic energy emitted from said transceiver and incident on said reflector back to said transceiver, and wherein said wire has two substantially parallel legs, a first of said legs being disposed to traverse said acoustic path between said transceiver and said reflector proximal said transceiver, and a second of said legs being disposed to transverse said acoustic path between said transceiver and said reflector proximal said reflector.

\* \* \* \* \*